United States Patent [19]

Imai

[11] 4,407,731

[45] Oct. 4, 1983

[54] PREPARATION OF METAL OXIDE-SUPPORTED BORON FLUORIDE CATALYSTS

[75] Inventor: Tamotsu Imai, Mount Prospect, Ill.

[73] Assignee: UOP Inc., Des Plaines, Ill.

[21] Appl. No.: 440,112

[22] Filed: Nov. 8, 1982

[51] Int. Cl.$^3$ ............................................. B01J 21/02
[52] U.S. Cl. ................................................... 502/203
[58] Field of Search ......................................... 252/433

[56] References Cited

U.S. PATENT DOCUMENTS

| | | | |
|---|---|---|---|
| 2,935,545 | 5/1960 | Bloch et al. | 252/433 X |
| 2,939,890 | 6/1960 | Hervert et al. | 252/433 X |
| 3,068,301 | 12/1962 | Hervert et al. | 252/433 X |

Primary Examiner—Delbert E. Gantz
Assistant Examiner—William G. Wright
Attorney, Agent, or Firm—James R. Hoatson, Jr.; Raymond H. Nelson; William H. Page, II

[57] ABSTRACT

Catalytic compositions of matter which are useful in oligomerization and alkylation reactions may be prepared by treating a metal oxide support such as alumina with an aqueous solution of an acid, washing the treated metal oxide with an aqueous solution of an alkaline compound followed by drying and calcining the support. The treated support which contains added hydroxyl groups on the surface thereof is then impregnated with boron trifluoride to form the desired catalyst. The catalyst which possesses a high activity may be used at lower reaction conditions to give comparable results of conversion and selectivity.

14 Claims, No Drawings

PREPARATION OF METAL OXIDE-SUPPORTED BORON FLUORIDE CATALYSTS

BRIEF SUMMARY OF THE INVENTION

Many olefinic hydrocarbons which contain from 4 to about 12 carbon atoms in the chain are utilized in various industries in many ways. In addition, alkylated hydrocarbons such as alkyl aromatics will also find a wide variety of uses. For example, one specific use of olefinic hydrocarbons such as those containing 8 carbon atoms in the chain is as a component in motor fuels such as internal combustion engines utilizing gasoline. The presence of these compounds in the motor fuel will improve the octane number of the fuel to a higher level, thus enabling the motor fuel such as gasoline to operate efficiently at this high octane number, either in the leaded or unleaded state. Another use of compounds such as the $C_8$ olefinic hydrocarbons would be as plasticizers, especially those olefinic hydrocarbons which possess a relatively straight chain configuration with a minimum of branching, such as only one or two methyl substituents on the chain. The use of these compounds as plasticizers which, when added to a plastic, will facilitate the compound as well as improve the flexibility and other properties of the finished product. Examples of uses for olefinic hydrocarbons containing 6 carbon atoms would be in the synthesis of flavors, perfumes, medicines, dyes and resins, while olefinic hydrocarbons containing 12 carbons atoms in the chain may be used as intermediates in the preparation of detergents, lubricants, additives, plasticizers as well as in the synthesis of flavors, perfumes, medicines, oil, dyes, etc. In a like manner, alkyl aromatic compounds which have been prepared by the alkylation of aromatics such as benzene, toluene, etc. with an olefinic hydrocarbon precursor are also useful in many ways. For example, ethylbenzene will find use in organic synthesis, as a solvent or diluent as well as an intermediate in the production of styrene. Butylated benzenes such as tertbutylbenzene may be used in the sythesis of dyes, pharmaceuticals and other organic chemicals as well as in the manufacture of resins. Cymene (isopropyltoluene) is used as a solvent in metal polishers, in organic syntheses reaction, etc.

The preparation of these alkylated compounds as well as the olefinic hydrocarbons which are formed by the oligomerization of olefinic hydrocarbons containing from two to about six carbon atoms may be effected in the presence of a catalytic composition of matter comprising boron fluoride which is supported on a metal oxide.

As will hereinafter be shown in greater detail, by utilizing a specific novel method of preparing this catalyst, as opposed to other methods, it is possible to obtain a catalyst which is more active than previous catalysts and therefore, will be able to function at oligomerization or alkylation conditions which are lower than those previously used, thus resulting in a superior efficiency as well as reducing the overall cost of the oligomerization or alkylation reaction.

It is therefore an object of this invention to provide a process for preparing catalytic compositions of matter.

A further object of this invention is found in providing a process for preparing a more active catalyst which may be utilized in desired chemical reactions.

In one aspect an embodiment of this invention resides in a method for the preparation of a metal oxide-supported boron fluoride catalyst which comprises treating said metal oxide with an aqueous solution of an acid at treating conditions, washing the treated metal oxide with an aqueous solution of an alkaline compound, calcining the resultant treated metal oxide at calcination conditions, impregnating said treated metal oxide with boron trifluoride at impregnation conditions, and recovering the resultant metal oxide-supported boron fluoride catalyst.

A specific embodiment of this invention is found in a method for the preparation of a metal oxide-supported boron fluoride catalyst which comprises treating gamma-alumina with an aqueous solution of hydrochloric acid containing from about 1% to about 30% by weight of said hydrochloric acid at a temperature in the range from about ambient to about 100° C., washing the treated alumina with an aqueous solution of tetramethyl ammonium hydroxide, calcining the gamma-alumina at a temperature in the range of from about 200° to about 450° C., impregnating said gamma-alumina with gaseous boron fluoride at a temperature in the range of from about ambient to about 400° C. and recovering the resultant gamma-alumina-supported boron fluoride catalyst.

Other objects and embodiments may be found in the following further detailed description of the present invention.

DETAILED DESCRIPTION OF THE INVENTION

As hereinbefore set forth, the present invention is concerned with a process for preparing an improved catalyst which may be used in oligomerization and alkylation reactions. The catalyst comprises a metal oxide-supported boron fluoride compound which possesses increased activity over that which is present in catalysts which have been prepared according to other processes or methods. Other metal oxide-supported boron fluoride catalysts such as alumina-supported boron fluoride catalysts have been prepared by treating the support at an elevated temperature with boron trifluoride, usually in gaseous form, and recovering the impregnated support. In contradistinction to this, a metal oxide-supported boron fluoride catalyst may be prepared by treating the metal oxide prior to the impregnation of the boron fluoride thereon. In a catalyst of the nature of the present compound, the boron fluoride is supported on the surface of the base by reaction with surface hydroxyl groups of said base. Therefore, the amount of boron fluoride which is available for impregnation on said support is limited by the amount of available hydroxyl groups. By utilizing the process of the present invention, it has now been found possible to increase the number of hydroxyl groups on the surface of the support which are available for reaction with the boron fluoride and thus, the amount of said boron fluoride which will be present in the finished catalytic composition of matter will be greatly increased. This increase in the boron fluoride content of the catalyst will, in turn, lead to an increase in activity of the catalytic composition of matter, thereby permitting the catalyst to act in a more efficient manner at lower reaction conditions.

The metal oxide which is utilized as a base or support for the boron fluoride will comprise a high surface area metal oxide such as alumina, particularly gamma-alumina, eta-alumina, theta-alumina, etc., silica or silica-alumina. The term "high surface area" as used in the present specification will be defined as a surface area which ranges from 1 to about 500 m²/g.

The process of the present invention entails treating a metal oxide of the type hereinbefore set forth in a series of process steps to prepare the desired compound. The first step of the process entails treating the metal oxide such as gamma-alumina with an aqueous solution of an acidic compound, either inorganic or organic in nature, the concentration of said acid present in said aqueous solution ranging from about 0.1 to about 30% by weight. Examples of acids which may be employed in the treatment of the metal oxide base will include inorganic acids such as hydrofluoric acid, hydrochloric acid, hydrobromic acid, hydroiodic acid, nitrous acid, nitric acid, phosphorous acid, phosphoric acid, sulfurous acid, sulfuric acid, etc; organic acids such as formic acid, acetic acid, propionic acid, trichloroacetic acid, benzene sulfonic acid, toluene sulfonic acid, etc. It is to be understood that the aforementioned acids are merely representative of the type of acids which may be employed and that the present invention is not necessarily limited thereto. The treatment of the base with an aqueous solution of the aforesaid acid is effected at treatment conditions which will include a temperature in the range of from about ambient (20°-25° C.) up to about 100° C. or more for a period of time which may range from about 0.5 up to about 10 hours in duration.

Following the treatment of the metal oxide with the aqueous acidic solution, the treated metal oxide support is then washed with an aqueous solution of an alkaline compound, some specific examples of these compounds including sodium hydroxide, potassium hydroxide, lithium hydroxide, rubidium hydroxide, cesium hydroxide, magnesium hydroxide, calcium hydroxide, strontium hydroxide, barium hydroxide, ammonium hydroxide; quaternary ammonium salts such as tetramethyl ammonium hydroxide, tetraethyl ammonium hydroxide, tetrapropyl ammonium hydroxide, etc. The washing of the treated metal oxide support is also effected at elevated temperatures ranging from ambient to about 100° C. and preferably at the same temperature which was employed to treat the metal oxide with the aqueous acidic solution.

Again, the washing of the acid-treated metal oxide with the aqueous alkylate compound is effected for a predetermined period of time which may range from about 0.5 up to about 6 hours or more.

Following the treatment of the metal oxide support with the aqueous solution of the acid and the washing with an aqueous solution of an alkaline compound, the treated support is washed with an aqueous decomposable salt such as ammonium nitrate or alkaline compound such as ammonium hydroxide followed by wash with deionized water to remove any alkali or alkaline earth metal cations which may be present, the washing being effected by repeated treatments until the filtrate or washing water shows no such cations by analysis. Following the washing treatment, the treated support is dried at an elevated temperature in excess of about 100° C. and thereafter is calcined in an air atmosphere at a temperature which may range from about 200° to about 450° C. for a period of time which may range from 1 to 10 hours in duration.

The calcined treated support is then impregnated with boron trifluoride at temperatures which may range from about ambient to about 400° C., said impregnation preferably being effected in a pressure-resistant vessel such as an autoclave. After completing the charge of the gaseous boron trifluoride to the impregnation vessel which may take place during a period ranging from about 0.5 to about 6 hours or more in duration, the vessel and contents thereof are allowed to return to room temperature. Following the recovery of the metal oxide-supported boron fluoride catalyst, the catalyst may, if so desired, be further heated in an air or inert atmosphere such as nitrogen, helium, argon, etc. at a temperature which may range from about 100° to about 400° C. for a period of time which may range from up to about 6 hours to remove any traces of water or residual unwanted compound which may still have been present in the catalyst. Following the heat treatment, the catalyst may then be recovered and utilized in an oligomerization or alkylation reaction.

The process for producing the metal oxide-supported boron fluoride catalyst may be effected in any suitable manner. When utilizing a batch type operation, the metal oxide base such as an alumina may be placed in an appropriate apparatus and contacted with the aqueous solution of the acid and thoroughly admixed at a predetermined temperature for the desired period of time. Following this, the acid-treated metal oxide may then be separated from the aqueous acidic solution by conventional means such as filtration and added to an aqueous solution of an alkaline compound which is maintained at the proper operating temperature. After thorough admixing for a predetermined period, the metal oxide support is then separated from the alkaline solution, again by conventional means such as filtration, and subjected to a washing operation with water or an aqueous decomposable salt or alkaline compound followed by wash with water until the wash is neutral. If so desired, the spheres may then be treated with water for a period of time and thereafter filtered under vacuum to remove any excess water. Following this, the metal oxide support is then dried and calcined for a period of time at a temperature within the range hereinbefore set forth. The calcined metal oxide support is then placed in an appropriate apparatus such as an autoclave which is heated to the desired impregnation conditions. Thereafter, the gaseous boron fluoride is charged to the autoclave at a predetermined rate while maintaining the autoclave at the desired operating temperature. Upon completion of the addition of the boron trifluoride, heating is discontinued and the apparatus allowed to cool to room temperature. After recovery of the catalyst it may, if so desired, be further heated in an air atmosphere at an elevated temperature for a predetermined period of time and thereafter recovered.

When employing a continuous manner of operation, the metal oxide support may be continuously charged to a reaction vessel containing the aqueous acidic solution and, after passage through the vessel, it may then be continuously withdrawn and passed to a second reaction vessel wherein the metal oxide support is contacted with an aqueous solution of an alkaline compound, both of the vessels containing the aqueous acidic solution and the aqueous alkaline solution being maintained to the proper operating conditions of temperature and, if so desired, pressure. Again, after passage through the second vessel for a predetermined period of time, the metal oxide support is continuously withdrawn and washed to remove any traces of alkali or alkaline earth metal cations which may still be present. After continuous passage through the washing zone, the metal oxide support is passed through a drying and calcining zone to remove residual water and thereafter continuously charged to an impregnation zone wherein it is contacted with gaseous boron trifluoride, the boron trifluoride also being continuously charged to this impregnation zone. After passage through the impregnation zone which is maintained at the proper operating conditions of temperature and pressure, the metal oxide-supported boron fluoride catalyst is continuously withdrawn, cooled and recovered.

As hereinbefore set forth, the catalyst which has been prepared according to the process of the present invention may be utilized as an oligomerization or alkylation catalyst. As an illustration of one of the types of reaction, the catalyst may be employed in the oligomerization of an olefinic hydrocarbon such as propylene or butene by placing the catalyst in an appropriate apparatus such as a reaction flask, autoclave, etc. and charging the olefinic hydrocarbon which is to be oligomerized to said apparatus at predetermined reaction conditions which may include a temperature in the range of from about 50° to about 350° C., a pressure range from 50 to about 2000 psig and a Liquid Hourly Space Velocity ranging from about 0.5 to about 10. If so desired, the olefinic hydrocarbon which is to be oligomerized may be admixed with a paraffin which will act as a diluent for the reaction. Upon completion of the desired reaction period, which may range from about 0.5 up to about 10 hours or more in duration, the reaction mixture, after allowing the apparatus to return to room temperature and atmospheric pressure, is recovered. The desired products comprising the minimal branched oligomers are separated from the catalyst and unreacted olefins by conventional means such as fractional distillation and recovered.

As will hereinafter be shown in greater detail in the examples at the end of this specification, it is possible to effect the reaction such as oligomerization at less severe reaction conditions while maintaining high conversion and selectivity when employing the catalyst which has been prepared according to the process of this invention that can be effected when employing a catalyst which has been prepared in a dissimilar manner.

The following examples are given for purposes of illustrating the process of the present invention. However, it is to be understood that these examples are given merely for purposes of illustration and that the present process is not necessarily limited thereto.

EXAMPLE I

A catalyst was prepared according to the process of this invention by diluting 30 ml of concentrated hydrochloric acid with water to form a volume of 600 ml. This aqueous solution was added to 150 grams of gamma-alumina spheres in a vessel and the mixture was stirred for a period of one hour at a temperature of 60° C. The solution was filtered and the spheres were added to 600 ml of an aqueous solution containing 50.02 grams of tetramethylammoniumhydroxide while maintaining the temperature of the solution at 55° C. The solution was then heated to 60° C. and stirred for a period of one hour. At the end of this time, the spheres were filtered on a Buchner funnel and washed with water until the filtrate showed no precipitate when subjected to a silver nitrate solution. The spheres were then soaked in water for a period of 16 hours, washed again with water and filtered under vacuum to remove the excess water. The spheres were then dried in a furnace for a period of two hours at a temperature of 110° C., 182.02 grams of treated gamma-alumina being recovered after the drying. The spheres were then calcined at a temperature of 300° C. in an air atmosphere which was charged to the furnace at a rate of one liter per minute, the calcination being effected for a period of three hours. At the end of this time, 135.09 grams of treated gamma-alumina containing 0.02% by weight of chlorine were recovered.

The desired catalyst was then prepared by charging 127.8 grams of the calcined gamma-alumina spheres to a 1-liter autoclave which was then heated to a temperature of 300° C. in air at a pressure of 20 psig. Gaseous boron trifluoride in an amount of 60 grams was charged to the autoclave during a period of four hours while maintaining the temperature in a range of from 308° to 343° C. At the end of this period, heating was discontinued and the autoclave was allowed to cool to room temperature, 161.2 grams of catalyst being recovered. Analysis of this catalyst showed the presence of 12.3% by weight of fluorine and 3.12% by weight of boron on the catalyst. To remove any excess boron and fluorine, 100 cc (60.17 grams) was charged to a quartz tube and heated to a temperature of 350° C. in an air flow charged to the tube at a rate of 1-liter per hour. The temperature of the tube was controlled at a range of from 350° to 375° C. for a period of three hours, at the end of which time 54.29 grams were recovered. Analysis of the catalyst showed the presence of 10.8% by weight of fluorine and 2.2% by weight of boron, the physical characteristics of the catalyst including a surface area of 138 m$^2$/g, a pore volume of 4.40 ml/g and an average pore diameter of 116 Angstroms.

EXAMPLE II

In this example, a catalyst was prepared by subjecting about 1000 lbs. of gamma-alumina spheres which had been dried and calcined at a temperature of 620° C. for a period of 4 hours to gaseous boron trifluoride in a vessel at a temperature of 350° C. for a period of 5½ hours. Following the impregnation of the alumina with the boron trifluoride, the catalyst was recovered and dried at a temperature of 260° C. for a period of 1½ hours. Analysis of the catalyst after recovery thereof showed the presence of 7.8% by weight of fluorine and 1.8% by weight of boron.

EXAMPLE III

The catalysts which were prepared according to Examples I and II above were utilized as oligomerization catalysts for the treatment of butene-2. In each case, 50 cc of the catalyst composites were placed in a tubular stainless steel reactor. A feedstock consisting of 60% butene-2 and 40% n-butane was passed over the catalyst at a Liquid Hourly Space Velocity of 1.0 hour$^{-1}$ while maintaining a pressure of 1000 psig. Both catalysts showed stable activities during the tests; the results of the tests are set forth in Table I below. In the Table, the catalyst prepared according to the process of this invention was labeled A and the catalyst prepared in a conventional manner was labeled B.

TABLE I

|  | A | B |
|---|---|---|
| Hours on Stream | 492–504 | 216–276 |
| Temperature °C. | | |
| Inlet | 104 | 136 |
| Maximum | 119 | 150 |
| % Conversion | 60.4 | 60.4 |
| Selectivity | | |
| C$_6$ | 0.5 | 0.8 |
| C$_7$ | 0.5 | 0.6 |

TABLE I-continued

|  | A | B |
|---|---|---|
| $C_8$ | 78.0 | 79.1 |
| $C_9^+$ | 21.0 | 19.5 |
| $C_8^=$ Isomers | | |
| N—$C_8$ | — | — |
| $MeC_7$ | 1.2 | 2.8 |
| $DMC_6$ | 98.2 | 96.5 |
| $TMC_5$ | 0.6 | 0.7 |
| $C_8^=$ Yield | 47.1 | 47.8 |

It is noted from a comparison of the results set forth in the above Table that the catalyst prepared according to the process of the present invention exhibited comparable dimerization selectivities as well as octane isomer selectivities at a significantly lower operating temperature. This indicates that the catalyst of the present invention possesses a much higher activity than previous catalysts.

I claim as my invention:

1. A method for the preparation of a metal oxide-supported boron fluoride catalyst which comprises treating said metal oxide with an aqueous solution of an acid at treating conditions, washing the treated metal oxide with an aqeous solution of an alkaline compound, calcining the resultant treated metal oxide at calcination conditions, impregnating said treated metal oxide with boron trifluoride at impregnation conditions, and recovering the resultant metal oxide-supported boron fluoride catalyst.

2. The method as set forth in claim 1 in which said metal oxide is a high surface area alumina.

3. The method as set forth in claim 2 in which said high surface area alumina is gamma-alumina.

4. The method as set forth in claim 1 in which said treating conditions include a temperature in the range of from about ambient to about 100° C.

5. The method as set forth in claim 1 in which said calcination conditions include a temperature in the range of from about 200° to about 450° C.

6. The method as set forth in claim 1 in which said impregnation conditions include a temperature in the range of from about ambient to about 400° C.

7. The method as set forth in claim 1 in which said acid is present in said aqueous solution in an amount in the range of from about 1% to about 30% by weight.

8. The method as set forth in claim 7 in which said acid is hydrochloric acid.

9. The method as set forth in claim 7 in which said acid is nitric acid.

10. The method as set forth in claim 7 in which said acid is sulfuric acid.

11. The method as set forth in claim 1 in which said alkaline compound is sodium hydroxide.

12. The method as set forth in claim 1 in which said alkaline compound is potassium hydroxide.

13. The method as set forth in claim 1 in which said alkaline is tetramethylammoniumhydroxide.

14. The method as set forth in claim 1 in which said boron trifluoride which is present is gaseous boron trifluoride.

* * * * *